(12) United States Patent
Ahlmén et al.

(10) Patent No.: US 8,539,950 B2
(45) Date of Patent: Sep. 24, 2013

(54) METHOD AND APPARATUS FOR COLLECTION OF WASTE ANESTHETIC GASES

(75) Inventors: Christer Ahlmén, Sollentuna (SE); Stefan Broborg, Haninge (SE)

(73) Assignee: Maquet Critical Care AB, Solna (SE)

( * ) Notice: Subject to any disclaimer, the term of this patent is extended or adjusted under 35 U.S.C. 154(b) by 628 days.

(21) Appl. No.: 12/528,411

(22) PCT Filed: Feb. 27, 2007

(86) PCT No.: PCT/EP2007/051838
§ 371 (c)(1),
(2), (4) Date: Nov. 5, 2010

(87) PCT Pub. No.: WO2008/104218
PCT Pub. Date: Sep. 4, 2008

(65) Prior Publication Data
US 2011/0048417 A1     Mar. 3, 2011

(51) Int. Cl.
| | |
|---|---|
| A61M 15/00 | (2006.01) |
| A61M 16/00 | (2006.01) |
| A61M 16/10 | (2006.01) |
| A62B 7/10 | (2006.01) |
| A62B 19/00 | (2006.01) |
| A62B 23/02 | (2006.01) |
| A62B 27/00 | (2006.01) |
| A62B 9/02 | (2006.01) |
| G08B 3/00 | (2006.01) |
| G08B 5/00 | (2006.01) |
| B01D 59/26 | (2006.01) |

(52) U.S. Cl.
USPC ........... 128/205.12; 128/202.22; 128/203.12; 128/203.28; 128/205.24; 128/910; 95/90

(58) Field of Classification Search
USPC ........... 128/202.22, 203.12, 203.15, 203.22, 128/203.25, 203.28, 203.29, 204.18, 205.12, 128/205.23, 205.24, 205.27, 205.28, 205.29, 128/207.14, 207.16, 910
See application file for complete search history.

(56) References Cited

U.S. PATENT DOCUMENTS

| | | | |
|---|---|---|---|
| 4,265,239 A | | 5/1981 | Fischer, Jr. et al. |
| 4,653,493 A | | 3/1987 | Hoppough |
| 4,991,576 A | * | 2/1991 | Henkin et al. ........... 128/203.28 |

(Continued)

FOREIGN PATENT DOCUMENTS

| | | |
|---|---|---|
| EP | 1 142 602 | 10/2001 |
| GB | 1 230 045 | 4/1971 |
| GB | 1 302 468 | 1/1973 |
| GB | 2 060 404 | 5/1981 |

*Primary Examiner* — Jackie Ho
*Assistant Examiner* — Mark K Han
(74) *Attorney, Agent, or Firm* — Schiff Hardin LLP

(57) ABSTRACT

In an apparatus for collection of waste anesthetic gases, and a method of using such an apparatus, the apparatus has a gas collection chamber with an input port to be connected to an exhaust of an anesthesia delivery system for receiving a first gas flow therefrom that contains a waste anesthetic gas component. An output port from the gas collection chamber is connected to a vacuum system for evacuation of an evacuation gas flow from the gas collection chamber. A bidirectional port leads to and from the gas collection chamber, which has an adsorbing unit connecting the gas collection chamber with an ambient environment surrounding the gas collection chamber. The apparatus provides for safe prevention of discharge of exhaled anesthetic gases into an ambient atmosphere surrounding the apparatus.

17 Claims, 2 Drawing Sheets

(56) References Cited

U.S. PATENT DOCUMENTS

| | | | |
|---|---|---|---|
| 5,044,361 A | 9/1991 | Werner et al. | |
| 5,109,838 A * | 5/1992 | Elam | 128/203.12 |
| 5,678,540 A * | 10/1997 | Kock et al. | 128/205.13 |
| 5,694,924 A * | 12/1997 | Cewers | 128/204.21 |
| 5,950,623 A * | 9/1999 | Michell | 128/205.24 |
| 6,041,777 A * | 3/2000 | Faithfull et al. | 128/200.24 |
| 6,119,686 A * | 9/2000 | Somerson et al. | 128/202.22 |
| 6,799,570 B2 * | 10/2004 | Fisher et al. | 128/200.24 |
| 7,100,606 B2 * | 9/2006 | Fisher et al. | 128/204.18 |
| 2005/0112325 A1 * | 5/2005 | Hickle | 428/141 |

* cited by examiner

METHOD AND APPARATUS FOR COLLECTION OF WASTE ANESTHETIC GASES

BACKGROUND OF THE INVENTION

1. Field of the Invention

This invention pertains in general to the treatment of waste anesthetic gases from healthcare or other facilities that use inhaled anesthetics for medical or veterinary purposes. In particular, the invention pertains to a scavenging method and apparatus for collection of waste anesthetic gases produced by an anesthesia delivery system of the healthcare facility, such as a conventional anesthesia machine or a ventilator with sedation capabilities.

2. Description of the Prior Art

Anesthesia delivery systems, such as anesthesia machines in surgical facilities, both hospital and outpatient units, produce significant quantities of waste anesthetic gases. These gases are collected from the patients' exhalation by a central vacuum system. The healthcare facilities typically employ vacuum pumps to collect waste gases from anesthetizing locations. Waste anesthetic gases are pumped to the outside of the medical facility, where the gases are vented to the atmosphere outside the medical facility.

However, healthcare personnel operating the anesthesia machines, may omit to connect the anesthesia machine's exhaust to the central vacuum system. This may happen unintentionally by mistake, or intentionally, for instance during patient transport. In this case the stream of waste anesthetic gases from the anesthesia delivery system escapes to the ambient environment surrounding the anesthesia delivery system. This is undesired as the healthcare personnel is exposed to the waste anesthetic gases and likely breathes in and gets affected or harmed by these gases.

Moreover, vacuum systems have a limited evacuation capacity. When peak flows exit the anesthesia delivery system, as for instance may occur when ventilating the patient with large minute volumes, the gas flow exiting the anesthesia machine partly leaks out to the ambient environment thereof. This leakage has the same disadvantageous effect as cited above, because healthcare personnel is exposed to the leaking waste anesthetic gases.

U.S. Pat. No. 5,044,363 discloses adsorption of anesthetic gases from anesthesia delivery systems by charcoal granules. A cartridge loosely containing powdered activated charcoal is connected to an anesthetic administration system. Waste anesthetic gases are directed through the activated charcoal, achieving removal of approximately 95% of anesthetic substances that otherwise would be released. However, the cartridge described in U.S. Pat. No. 5,044,363 is of relatively large size and devised for facilities that lack a central vacuum system. Furthermore, the cartridge does not provide information about its remaining efficiency and has to be regularly replaced by a fresh cartridge, which is less economical. It is also difficult to determine when a replacement is needed without risking the leakage of anesthetic gas. Moreover, the cartridge has a rather large flow resistance, which is disadvantageous for most anesthesia machines as a pressure is built up upstream the cartridge. This may deteriorate the performance of the anesthesia machine as for instance the regulation of an expiratory pressure is rendered more difficult. Also, the cartridge may leak at high flow rates, as described above.

EP-A2-1142602 discloses an anesthetic gas filter for connection to an anesthesia delivery system and for absorbing or adsorbing anesthetic gas. The anesthetic gas filter has an inlet and an outlet, as well as an adsorbing or absorbing material arranged between the inlet and the outlet of the anesthetic gas filter. The inlet of the anesthetic gas filter is to be connected to an anesthetic machine in order to receive expired gas. The outlet of the anesthetic gas filter is either open or connected to an evacuation line. Thus, the expired gas received from the anesthesia machine into the anesthetic gas filter is always led through the adsorbing or absorbing material of the anesthetic gas filter. Hence, the adsorbing or absorbing material of the anesthetic gas filter is consumed or loaded at every exhalation, constantly deteriorating the efficiency of the anesthetic gas filter in use. The anesthetic gas filter further comprises an anesthetic gas detector arranged in the anesthetic gas filter, such that an early indication of the need to replace the anesthetic gas filter is provided. A replacement of the filter has to be done frequently as the entire anesthetic waste gas is lead through the filter under all operating conditions of the disclosed anesthesia machine. Furthermore, the expiratory resistance added by the anesthetic gas filter to the expiratory branch under all operating conditions, even when connected to an evacuation line, is disadvantageous. The resistance of an expiratory channel is desired to be as low as possible.

Hence, an improved method and apparatus for preventing waste anesthetic gases from escaping to the ambient environment surrounding an anesthesia machine, connectable to a vacuum system, would be advantageous and in particular allowing for increased flexibility and/or cost-effectiveness.

SUMMARY OF THE INVENTION

According to one aspect of the invention, an apparatus for collection of waste anesthetic gases is provided. The apparatus has a gas collection chamber that has a first port, a second port, and a third port. The first port is an input port to the gas collection chamber, and the input port is adapted to be in fluid communication with an exhaust of an anesthesia delivery system and is arranged to receive a first gas flow from the anesthesia delivery system, this first gas flow including a waste anesthetic gas component, for instance a volatile anesthetic agent previously vaporized into the first gas flow. The first gas flow may be an exhalation gas flow from a patient sedated by means of the anesthetic agent delivered by the anesthesia delivery system. The second port is an output port from the gas collection chamber, and the output port is adapted to be in fluid communication with a vacuum system for evacuation of an evacuation gas flow from the gas collection chamber. The third port is a bidirectional port leading to and from the gas collection chamber. The bidirectional port contains an adsorbing unit, and places the gas collection chamber in fluid communication with an ambient environment surrounding the gas collection chamber.

According to another aspect of the invention, a method is provided for scavenging a waste anesthetic gas component from an exhaust gas flow from an exhaust of an anesthesia delivery system. The method includes receiving the gas flow from the anesthesia delivery system into a gas collection chamber of an apparatus for collection of waste anesthetic gases through an input port to the gas collection chamber, the input port being in fluid communication with the exhaust of the anesthesia delivery system. A directed gas flow to or from the gas collection chamber is provided through a bidirectional port in fluid communication with an ambient environment surrounding the gas collection chamber and including an adsorbing unit, depending on the exhaust gas flow and an evacuation gas flow from the gas collection chamber through an output port from the gas collection chamber to a vacuum system.

Some embodiments of the invention provide for preventing release of gases or vaporized anesthetic substances into the ambient atmosphere in facilities where such substances are used.

Some embodiments of the invention also provide for an indication that a vacuum system is not connected.

Some embodiments provide for temporarily disconnecting an anesthesia machine from a central vacuum system, e.g. for patient transport, and still preventing egress of exhaled anesthetic gases into the ambient atmosphere.

Some embodiments provide for a small size compact unit having long service life and still reliably preventing egress of exhaled anesthetic gases into the ambient atmosphere.

It should be emphasized that the term "comprises/comprising" when used in this specification is taken to specify the presence of stated features, integers, steps or components but does not preclude the presence or addition of one or more other features, integers, steps, components or groups thereof.

DESCRIPTION OF THE PREFERRED EMBODIMENTS

Figure 1:
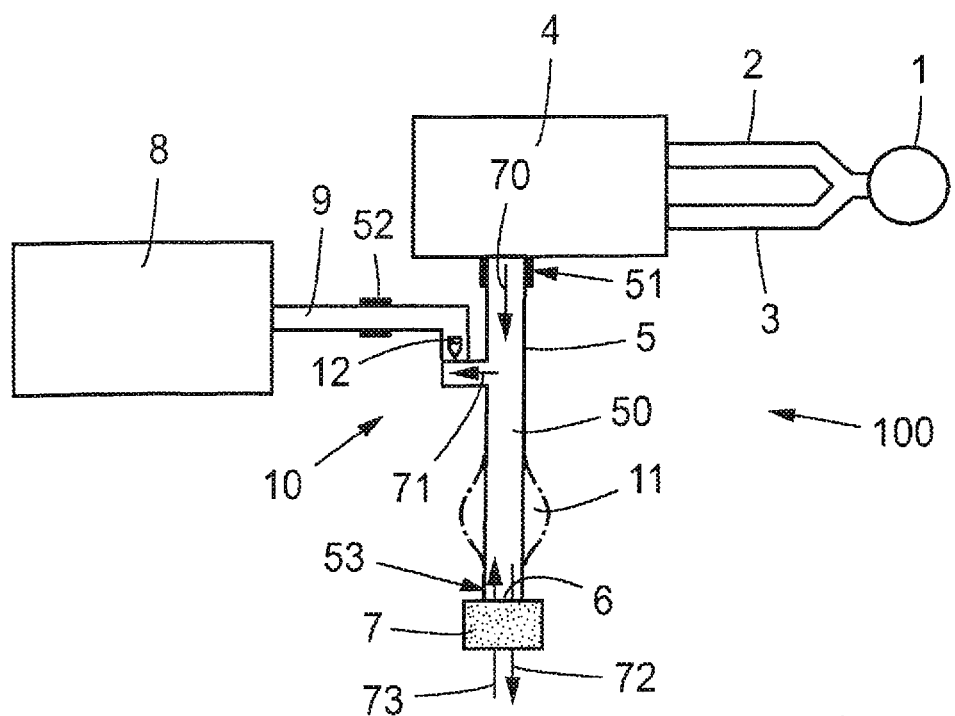
FIG. 1 is a schematic illustration of an anesthesia machine connected to a vacuum system, having an apparatus for collection of waste anesthetic gases.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements or features.

The following description focuses on embodiments of the present invention applicable to an anesthesia machine. However, it will be appreciated that the invention is not limited to this application but may be applied to many other breathing apparatuses, including for example medical respirators that may deliver volatile anesthetic agents to a patient.

FIG. 1 is a schematic illustration of an anesthesia delivery system in form of an anesthesia machine 4 connected to a vacuum system 8, having an apparatus 100 for collection of waste anesthetic gases from the anesthesia machine 4.

A patient 1, which is shown schematically, is connected to the anesthesia machine 4 via an inspiration tube 2 and an expiration tube 3. By way of the anesthetic machine 4, an anesthetic agent is delivered to the patient 1 through inspiration tube 2, usually vaporized in a carrier gas mixture comprising oxygen, air and/or nitrous oxide. Anesthetic agents commonly used are well known types of halogenated hydrocarbons which include anesthetic agents known under the trademarks isoflurane, enflurane, halothane, sevoflurane and desflurane. As the patient breathes the gas stream containing the anesthetic agent, a desired degree of unconsciousness is achieved. Only a very low fraction of the inhaled anesthetic is absorbed into the blood stream of patient 1. The exhaled gas thus contains almost all the anesthetic administered to the patient. As mentioned above, it is of importance to ensure that the gas exhaled by the patient 1 through expiration tube 3 is not exhausted into the ambient environment surrounding the anesthesia machine, e.g. an operating theatre or an emergency room, because the presence of the anesthetics may affect personnel in the ambient environment. This is in particular of importance if the anesthesia machine is operated as an open system, i.e. the exhaled patient gas is not recycled through a $CO_2$ absorber and returned to the patient, but directly exhausted from the anesthesia machine. In this case large minute volumes of waste anesthetic gases leave the anesthesia machine and have to be taken care of. Embodiments of the apparatus for collection of waste anesthetic gases from an anesthesia machine provide collection of a large range of minute volumes of such waste anesthetic gases. Some embodiments provide for automatic adaptation to different minute volumes of waste anesthetic gases, e.g. when switching the anesthesia machine from a closed system operation to an open system operation.

Apparatus 100 for collection of waste anesthetic gases from an anesthesia machine 4 comprises a flexible tube 5 enclosing a gas collection chamber 50 in its interior. Gas collection chamber 50 has a first port, a second port, and a third port.

The first port is an input port 51 to the gas collection chamber 50. The input port 51 is fluidly connectable to an exhaust of an anesthetizing machine 4. In the use of apparatus 100, input port 51 is connected to an exhaust port of the anesthesia machine 4 by suitable means, such as flexible tubing, other hardware plumbing known in the art, or directly via a suitable mechanical fluid connector comprising a suitable fastening element, e.g. connected to a standard anesthetic waste gas connector of the anesthesia machine 4. Input port 51 is thus arranged to receive an exhaled gas flow 70 discharged from anesthesia machine 4 through the exhaust port thereof. In operation of anesthesia machine, the gas stream therefrom includes a waste anesthetic gas component that originates from patient exhalation.

The second port is an output port 52 leading from the gas collection chamber 50. Output port 52 may be provided with a safety valve ensuring that gas only exits through the output port 52, but does not enter the gas collection chamber through the latter. The output port 52 is fluidly connectable to the central vacuum system 8, for instance via an exhaust tube 9. Thus a flow path for an evacuation gas flow 71 from chamber 50 is provided via output port 52. A flowmeter 10 may be arranged in the exhaust tube 9 in order to indicate the flow of gas evacuated into the vacuum system 8. The function of flowmeter 10 is explained below with reference to FIG. 2 and FIG. 3.

The third port is a bidirectional port 53 to and from the gas collection chamber 50. The bidirectional port 53 comprises an adsorbing unit 7 fluidly connecting the gas collection chamber 50 to an ambient environment surrounding the gas collection chamber 50. In such a manner an output gas flow 72 may leave the gas collection chamber 50, passing through the adsorbing unit 7. Adsorbing unit adsorbs any anesthetic agents in output gas flow 72. Hence, the stream of gas exhausted through port 53 is free of an anesthetic agent.

Output gas flow 72 leaves the collection chamber 50 for instance when vacuum system 8 is not capable of receiving the entire exhaled flow 70 entering chamber 50 through input port 51. Also, when no vacuum system 8 is connected to output port 52, the entire gas flow entering gas chamber 50 through input port 51 leaves the gas collection chamber via the bidirectional port 53. This may be ensured by suitable arrangements seeing to that output port 52 is closed when no vacuum system is connected to it or when vacuum system 8 is connected, but out of function. On the other hand, a flow 73 may enter gas collection chamber 50 through adsorbing unit 7 via the bidirectional port 53. This may occur when vacuum system provides a too high negative pressure creating a negative pressure in gas chamber 50, or during inspiration periods of patient 1, i.e. when no exhaled gas enters gas collection chamber through port 51. In this case gas entering gas collection chamber 50 with gas flow 73 leaves the latter through output port 52 with evacuation gas flow 71.

In a first mode of operation of apparatus 100, exhaled gases from the patient 1 are conducted from the anesthesia machine 4 to the vacuum system 8, such as a central vacuum and scavenging system in a hospital. More precisely, gas flow containing waste anesthetic gas enters gas collection chamber 50, and is buffered therein. From gas collection chamber 50 the gas comprising waste anesthetic gas exits through the output port 52 in evacuation gas flow 71, e.g. via exhaust tube 9. In this first mode of operation, there is substantially no input gas flow 73 via the bidirectional port 53 into the gas collection chamber 50 during exhalation, provided that the exhaled gas flow 70 is substantially equal to the evacuation gas flow 71.

However, in a second mode of operation, evacuation gas flow 71 is lower than exhaled gas flow 70. This may for instance occur when patient 1 is ventilated with high minute volumes. In this case the gas volume exhaled and conducted through expiration tube 3 to the gas collection chamber 50 inside flexible tubing 5 in exhaled gas flow 70 is high. Under these conditions the central vacuum system 8 may be overloaded and is not capable of evacuating the entire exhaled gas from flexible tubing 5 via output port 52. In this case the flexible tubing 5 is filled with the exhaled gas and the gas is exhausted from the flexible tubing 5 at the bidirectional port 53. This may also occur when vacuum system 8 is defect or disconnected. Bidirectional port 53 is provided as an open end 6 in flexible tube 5 and reaches the ambient environment. Bidirectional port 53 has attached the adsorbing filter 7 thereto in such a manner that the exhaled gas is guided through the adsorbing filter 7. Adsorbing filter 7 comprises an adsorbing agent, such as activated charcoal or a zeolite material. In this way, the anesthetic contained in the exhaled gas is adsorbed in the adsorbing filter 7 from output gas flow 72 and does at least partly not reach the ambient environment surrounding apparatus 100. In case of a fresh or regenerated adsorbing filter, substantially all anesthetic contained in the exhaled gas may becomes adsorbed in the adsorbing filter 7 from output gas flow 72. Depending on the absorbance capacity and the current degree of saturation of adsorbing filter 7, a part of the anesthetic contained in the exhaled gas may not be adsorbed in the adsorbing filter 7. However, during normal operation of the apparatus 100, at least a substantial part of the anesthetic is prevented from escaping to the surrounding environment by means of the embodied apparatus.

In a third mode of operation, gas is directed from bidirectional port 53 to output port 52, provided that vacuum system 8 is connected and in operation. This may for instance occur during an inspiration phase subsequent an expiration phase, or a phase with lower minute volumes, the central vacuum system 8 has excess capacity to empty the gas collection chamber 50 inside flexible tubing 5. Ambient air will be sucked into the flexible tubing 5 through adsorbing unit 7 in bidirectional port 53 as input gas flow 73. Thanks to the ambient air flushing through the adsorbing filter 7, the anesthetic agent adsorbed thereto is desorbed from the adsorbing filter 7 and transported together with the input gas flow 73 of ambient air into the gas collection chamber 50. From gas collection chamber 50 the gas diluted with ambient air from input gas flow 73 enters the central vacuum system 8 through output port 52 via the flexible tubing 5. The adsorbing filter 7 thus becomes regenerated by the input flow 73 reversed to output gas flow 72. The regeneration cycle of adsorbing and desorbing the anesthetic agent from adsorbing unit 7 may thus frequently be repeated, i.e. during every inspiration expiration cycle. Due to this fact the adsorbing unit may be of much smaller size than known adsorbing filters, such as known from EP-A2-1142602, which are replaced instead of regenerated. Furthermore, the adsorbing unit 7 has a longer time of service than conventional adsorbing filters, as the adsorbing unit 7 is intermittently or constantly cleaned or regenerated by input gas flow 73.

As mentioned above, adsorbing unit 7 contains an adsorbing agent that may be chosen from any of a variety of adsorbents. Adsorbing unit 7 may be provided in form of a replaceable or fixed filter cartridge. The filter cartridge contains the adsorbing agent. The adsorbing agent may be activated charcoal, for instance arranged in a porous fabric or wool, or loosely packed powdered activated charcoal material held between a suitable filter material at each end of the aforementioned filter cartridge.

Adsorbing unit 7 may contain a bed of hydrophobic molecular sieve adsorbent, such as of the high silica zeolite type. Such adsorbent has pore diameters large enough to permit molecules of anesthetic agents in the form of halogenated hydrocarbons to pass therethrough and be selectively adsorbed in the large internal cavities of the crystal framework, whereby the halogenated hydrocarbons are removed.

The flexible tubing 5 may have a resiliently elastic wall portion, for instance forming a balloon portion 11, as indicated by the dashed and dotted lines in FIG. 1. In this manner the flexible tubing 11 is capable of receiving a larger volume of expired gas and the expiratory resistance decreases.

Figure 2:
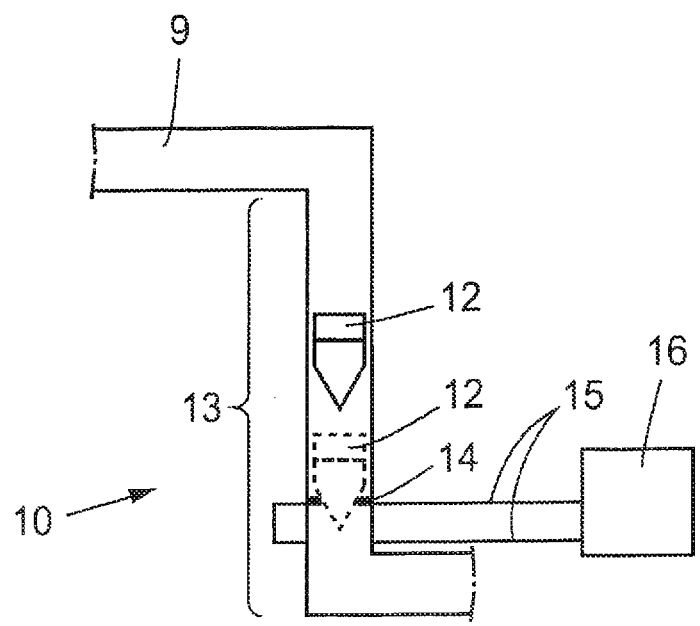
FIG. 2 is a schematic drawing illustrating a flowmeter shown in FIG. 1 in more detail.

The flowmeter 10, which may be comprised in apparatus 100, is shown in more detail in FIG. 2. Flowmeter 10 comprises a vertically arranged rigid transparent portion 13 above a seat 14 for a floating body 12. Floating body 12 may freely back and forth in the transparent portion 13, wherein the latter may be a portion of exhaust tube 9, or fluidly connected thereto. The flowmeter 10 may be arranged in the exhaust tube 9 in order to indicate the flow of gas evacuated into the vacuum system 8. The flowmeter 10 may also have an adjustable valve portion used to adjust a maximum flow that may pass through exhaust tube 9. A flowmeter of this type is for instance a rotameter. A desired flow may be adjusted visually by the position of floating body 12 in the transparent portion 13.

The flowmeter 10 may optionally include an integrated safety valve. Alternatively a separate safety valve may be incorporated into the output port 52 or tubing 9 connecting output port 52 with the vacuum system 8. For instance, in case operating personnel forgets to connect the exhaust tube to vacuum system 8, the safety valve is configured to prevent a gas flow of waste anesthetic gas through exhaust tube 9 to the ambient environment. By both providing the safety valve and the above named adsorption unit 7, it is ensured that waste anesthetic gas cannot egress from gas collection chamber 50 to ambient environment without having harmful anesthetic agents removed therefrom in adsorption unit 7—in case vacuum system 8 is not operating or not connected via exhaust tube 9.

According to an embodiment the apparatus 100 may comprise an alarm unit 16 which alarms operating personnel when the safety valve is closed. In this manner an indication may be given to operating personnel that vacuum system 8 is non operative or that exhaust tube 9 is disconnected there from. If this condition is not desired, which it might be, e.g. for patient transport with anesthesia machine 4 operative, the faulty condition is may be taken care of immediately.

Figure 3:
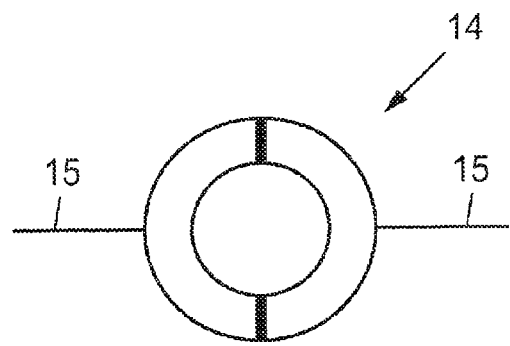
FIG. 3 is a plan view of the flow meter shown in FIG. 1 and FIG. 2.

The alarm unit 16 may be implemented as further illustrated in FIG. 3. The valve seat 14 is divided into two sections that are electrically isolated from each other. When floating body is at least partly, i.e. at the portion coming to rest against valve seat 14, made of an electrically conducting material, such as metal, the two sections of valve seat 14 may be short circuited and a signal may be conducted in a closed electrical circuit via electrical leads 15 to the alarm unit 16. More precisely, the two sections are short circuited when the floating body 12 rests against valve seat 14. This is the case when there is no gas flow to the vacuum system from gas collection chamber 50. The floating body 12 sealingly engages the valve seat 14 and prevents a gas flow into gas collection chamber 50 via the output port 52. That means the above-mentioned safety valve is provided as an integrated unit in the flowmeter 10. This results in exhaled gas flow 50 exiting the gas collection chamber 50 via the bidirectional port 53 through the adsorbing unit 7. As the adsorbing unit 7 has a certain flow resistance, a pressure increase is caused in gas collection chamber 50. In a practical embodiment, the flow resistance of adsorbing unit 7 may be in the range of 1-2 cm $H_2O$ at a throughput flow of approximately 60 l/min, or 3-4 cm $H_2O$ at a throughput flow of approximately 100 l/min. The actual flow resistance depends on the implementation of the adsorption unit 7, for instance depending on the surface area, thickness or volume thereof. In order to compensate for this pressure increase and in order to ensure proper function of apparatus 200, the weight of floating body 12 is chosen such that the safety valve does not open at normal operating pressures in gas collection chamber 50. Alternatively, in case the optional flowmeter 10 is not implemented, a safety valve may be provided having the above described safety valve and/or alarm functionality.

Now, the anesthesia machine 4 may be used without risk of contaminating operating personnel until the exhaust tube 9 reconnected to vacuum system 8. In case of long-term disconnections of exhaust tube 9 from the vacuum system 8, the adsorbing unit 7 may be exchanged to a fresh one. The need of replacing adsorbing unit may be determined in a number of different ways, e.g. by a color indicator proportional to the contaminant load of adsorbing unit 7, or by a anesthesia gas sensor measuring the concentration of anesthetic agent in gas flow 72 exiting the bidirectional port 53 through the adsorbing unit 7.

Alternatively, a separate safety valve (not illustrated) may be incorporated into the output port 52 or tubing 9 connecting output port 52 with the vacuum system 8. For instance, a safety valve may be provided that automatically closes output port 52 when no evacuation tube is connected thereto. Alternatively, the end of tubing 9 which is connected to a vacuum system manifold may be provided with this function, i.e. a safety valve closing off the passage through tubing 9 when the vacuum system is not connected. The safety valve may also be provided as a pressure release safety valve at the positions in apparatus 100 or 200, which is activated by a non-existing vacuum pressure, e.g. when vacuum system 8 is defective.

Figure 4:
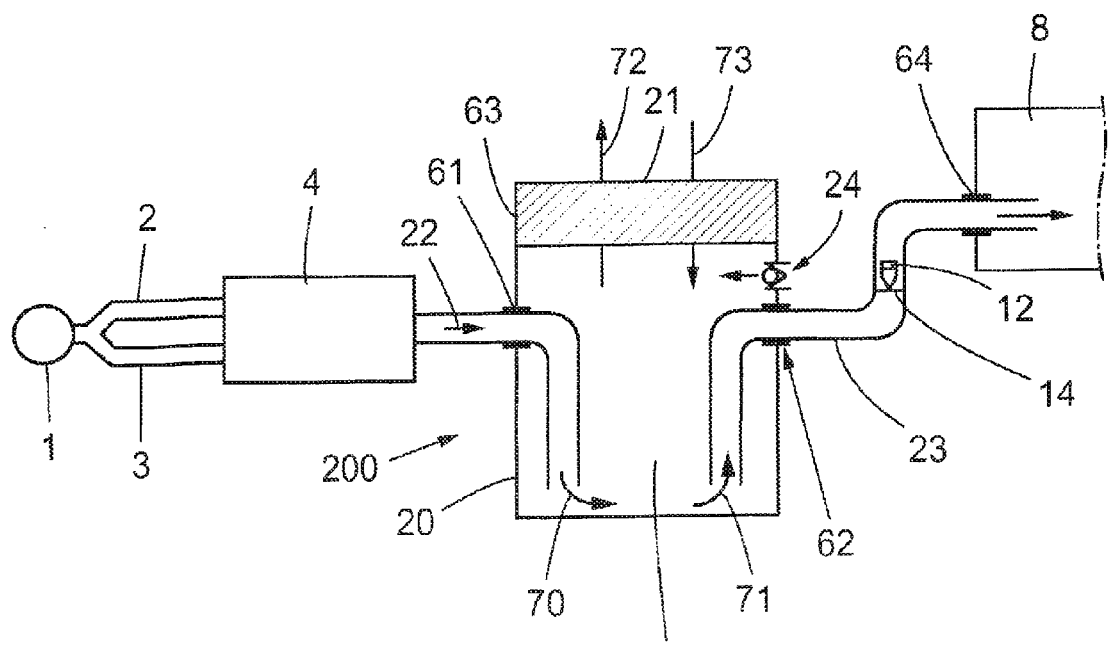
FIG. 4 is a schematic drawing illustrating an anesthesia machine connected to a vacuum system, comprising another apparatus for collection of waste anesthetic gases.

FIG. 4 is a schematic drawing illustrating an anesthesia machine 4 connected to a vacuum system 8, comprising a further embodiment of an apparatus 200 for collection of waste anesthetic gases. Apparatus 200 comprises a receptacle in form of a rigid container 20 having a gas collecting chamber 60 in its interior. Gas collection chamber 60 has a first port, a second port, and a third port. The first port is an input port 61 to said gas collection chamber 60. The second port is an output port 62 from said gas collection chamber 60. The third port is a bidirectional port 63 to and from the gas collection chamber 60. Ports 61, 62, 63 have the same functions as ports 51, 52, 53 of apparatus 100, respectively. An adsorbent unit 21 is provided in bidirectional port 63. As can be seen in FIG. 4, exhaled gas flow 70, evacuation gas flow 71, as well as output gas flow 72 and input gas flow 73 also are provideable by apparatus 200 in accordance with the above description. A tube 22 may connect input port 63 to anesthesia machine 4. An evacuation tube 23 may connect output port 62 to the vacuum system 8. A flowmeter 12 having a seat 14, maybe combined with a safety valve, may be provided in tube 23. Alternatively the second port is an output port 64 positioned downstream a flowmeter from the gas collection chamber 60, as illustrated in FIG. 4, instead of output port 62.

Apparatus 200 provides for easy mechanical installation of container 20, which may cost effectively be produced from a suitable plastic material.

Apparatus 200 may further have a mechanical vacuum breaker 24 fluidly coupled to the gas collecting chamber 60 as a safety measure. This vacuum breaker may be provided as a check valve opening when a too high negative pressure is generated in gas collection chamber 60 by vacuum system 8. This may occur under certain operating conditions, e.g. when adsorbing unit 21 creates a too high pressure drop over the adsorbing unit 21 when an input flow 73 is sucked into gas collection chamber 60. When an expiration valve of anesthesia machine is completely closed at the end of expiration, this is not an issue. However, when a positive end expiratory pressure (PEEP) is to be maintained by anesthesia machine 4, regulation of this PEEP may influenced by a too negative pressure in gas collection chamber 60, especially at low tidal volumes of patient 1. In this case vacuum breaker 24 opens against ambient atmosphere at a predefined threshold value. This predefined threshold is chosen in dependence on the flow resistance of adsorbing unit 7, as described above. The vacuum breaker is devised to open at a differential pressure between the gas collection chamber 60 and ambient atmosphere that is slightly higher than the flow resistance of adsorbing unit 7. In a practical implementation, the vacuum breaker is chosen to open at a negative pressure of 3-4 cm $H_2O$ in the gas collection chamber 60 with reference to ambient atmosphere, provided a nominal pressure drop of 2 cm $H_2O$ across adsorbing unit 7.

Alternatively to vacuum breaker 24, the adsorbing unit 21 may be devised to open at the predefined threshold pressure in order to provide the same effect as vacuum breaker 24. Adsorbing unit 21 may be suspended suitably such that the unit opens a fluid passage at the predefined threshold pressure, which passes the adsorbing agent and allows for free passage of atmospheric air into gas collection chamber 60. In accordance with this reasoning, it is envisaged that other embodiments, such as the embodiment shown in FIG. 1, have a similar vacuum breaker feature.

In addition to the above mentioned anesthetic agents in the form of halogenated hydrocarbons, the adsorbing unit may also to a certain extent adsorb other anesthetic agents. For instance nitrous oxide may to a certain extent be adsorbed in an adsorbing unit of certain embodiments. When nitrous oxide is used as a carrier gas for respiratory anesthesia, there are however rather large volumes to be handled by the adsorbing unit. In this case, the volume of an adsorbing material provided in the adsorbing unit, has to be adapted accordingly, depending on the specific anesthetic gas components or combination thereof, and to which extent these are desired to be prevented from entering the surrounding environment of the apparatus for collection of waste anesthetic gases.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Although modifications and changes may be suggested by those skilled in the art, it is the intention of the inventors to embody within the patent warranted heron all changes and modifications as reasonably and properly come within the scope of their contribution to the art.

We claim as our invention:

1. An apparatus to collect waste anesthetic gases from an exhaust gas flow from an exhaust of an anesthesia delivery system, said apparatus comprising:
    a gas collection chamber having a first port, a second port, and a third port;
    said first port forming an input port to said gas collection chamber, said input port being configured for fluid connection to an exhaust of said anesthesia system to receive a first gas flow discharged from said anesthesia delivery system, said exhaust gas flow including a waste anesthetic gas component;
    said second port forming an output port from said gas collection chamber, said output port being configured for fluid connection to a vacuum system for evacuation of an evacuation gas flow from said gas collection chamber; and
    said third port being a bidirectional port to and from said gas collection chamber, said bidirectional port having a regenerative adsorbing unit located therein that adsorbs or desorbs said waste anesthetic gas component dependent on gas flow through said regenerative adsorbing unit, said bidirectional port placing said gas collection chamber in fluid communication with an ambient environment surrounding said gas collection chamber allowing an output gas flow to exit from said gas collection chamber through said regenerative adsorbing unit with said waste anesthetic gas component being adsorbed by said regenerativer adsorbing unit, and said bidirectional port allowing a regenerative ambient air input gas flow to enter into said gas collection chamber through said regenerative adsorbing unit, causing said waste anesthetic gas component to be desorbed from said regenerative gas adsorbing unit and to exit said gas collection chamber through said output port together with said evacuation gas flow.

2. An apparatus as claimed in claim 1 wherein said gas collection chamber is formed inside a rigid receptacle.

3. An apparatus as claimed in claim 1 wherein said gas collection chamber is formed inside a flexible tubing.

4. An apparatus as claimed in claim 3 wherein said flexible tubing has a flexible wall section that is resiliently elastic, allowing variation of a volume in said gas collection chamber.

5. An apparatus as claimed in claim 1 wherein said regenerative adsorbing unit comprises a negative pressure release valve that places said gas collection chamber in fluid communication with said ambient environment when a negative pressure in said gas collection chamber is below a predetermined threshold.

6. An apparatus as claimed in claim 5 wherein said negative pressure release valve is releasably attached to said bidirectional port and, when said negative pressure exists in said gas collection chamber that is below said predetermined threshold, releases said regenerative adsorbing unit from said bidirectional port and places said gas collection chamber in fluid communication directly with said ambient environment.

7. An apparatus as claimed in claim 5 wherein said negative pressure release valve is a mechanical vacuum breaker fluidly coupled with said gas collection chamber.

8. An apparatus as claimed in claim 7 wherein said predetermined threshold value is dependent on a flow resistance of said regenerative absorbing unit, and wherein said vacuum breaker opens at a differential pressure between said gas collection chamber and said ambient atmosphere that is higher than said flow resistance of said regenerative adsorbing unit.

9. An apparatus as claimed in claim 8 wherein said predetermined threshold is a negative pressure in a range between 3 and 4 cm $H_2O$ in said gas collection chamber, with reference to said ambient atmosphere.

10. An apparatus as claimed in claim 1 wherein said second port comprises a safety valve that prevents gas flow out of said gas collection chamber through said second port when said vacuum system is not operating or not connected to said gas collection chamber.

11. An apparatus as claimed in claim 10 wherein said second port comprises a flow adjusting unit that indicates or adjusts said evacuation gas flow.

12. An apparatus as claimed in claim 10 comprising an alarm unit that emits a humanly perceptible indication that said safety valve is closed.

13. An apparatus as claimed in claim 12 wherein said safety valve comprises a valve seat divided into at least two sections that are electrically isolated from each other, and a floating body at least partially comprised of an electrically conductive material, said floating body being configured to rest against said valve seat when no evacuation gas flow exits from said gas collection chamber, and that short circuits said sections of said valve seat, to close an electrical circuit that triggers emission of said indication by said alarm unit, to indicate that said safety valve is closed.

14. An apparatus as claimed in claim 1 wherein said bidirectional port comprises a single opening to said ambient environment, said regenerative adsorbing unit being located in said single opening.

15. A method to collect waste anesthetic gases from an exhaust gas flow from an exhaust of an anesthesia delivery system having a gas collection chamber having a first port, a second port, and a third port, said method comprising the steps of:

using first port as an input port to said gas collection chamber, and placing said input port in fluid connection with an exhaust of said anesthesia system and receiving, via said input port, a first gas flow discharged from said anesthesia delivery system, said exhaust gas flow including a waste anesthetic gas component;

using said second port as an output port from said gas collection chamber, and placing said output port in fluid connection to a vacuum system and, from said output port, evacuating an evacuation gas flow from said gas collection chamber; and said third port being a bidirectional port to and from said gas collection chamber, and placing a regenerative adsorbing unit in said bidirectional port and, with said regenerative adsorbing unit, adsorbing or desorbing said waste anesthetic gas component dependent on gas flow through said regenerative adsorbing unit, and via said bidirectional port, placing said gas collection chamber in fluid communication with an ambient environment surrounding said gas collection chamber allowing an output gas flow to exit from said gas collection chamber through said regenerative adsorbing unit with said waste anesthetic gas component being adsorbed in said regenerative adsorbing unit, and via said bidirectional port, allowing a regenerative ambient air input gas flow to enter into said gas collection chamber through said regenerative adsorbing unit, causing said waste anesthetic gas component to be desorbed from said regenerative gas adsorbing unit and to exit said gas collection chamber through said output port together with said evacuation gas flow.

16. A method as claimed in claim 15 wherein gas flow through said bidirectional port is said output gas flow from said gas collection chamber through said bidirectional port to said ambient environment when said evacuation gas flow is less than said exhaust gas flow, causing said anesthetic agent in said waste anesthetic gases to be adsorbed by said regenerative adsorbing unit.

17. A method as claimed in claim 15 wherein gas flow through said bidirectional port is said input gas flow into said gas collection chamber through said bidirectional port from said ambient environment when said evacuation gas flow exceeds said exhaust gas flow, causing an anesthetic agent in said waste anesthetic gases to be desorbed from said regenerative absorbing unit, and evacuated to said vacuum system together with said evacuation gas flow.

\* \* \* \* \*